United States Patent
Tong et al.

(10) Patent No.: US 10,687,732 B2
(45) Date of Patent: Jun. 23, 2020

(54) SELECTING SLICE CONFIGURATION OF MEDICAL IMAGING APPARATUS

(71) Applicant: SHANGHAI NEUSOFT MEDICAL TECHNOLOGY CO., LTD., Shanghai (CN)

(72) Inventors: Lixia Tong, Shenyang (CN); Shanshan Lou, Shenyang (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 98 days.

(21) Appl. No.: 15/711,904

(22) Filed: Sep. 21, 2017

(65) Prior Publication Data

US 2018/0078167 A1 Mar. 22, 2018

(30) Foreign Application Priority Data

Sep. 22, 2016 (CN) .......................... 2016 1 0844028

(51) Int. Cl.
*A61B 5/055* (2006.01)
*A61B 6/03* (2006.01)
*A61B 6/00* (2006.01)
(Continued)

(52) U.S. Cl.
CPC ................. *A61B 5/055* (2013.01); *A61B 6/03* (2013.01); *A61B 6/542* (2013.01); *A61B 6/545* (2013.01);
(Continued)

(58) Field of Classification Search
CPC ......... A61B 5/055; A61B 6/545; A61B 6/542; A61B 6/03; G06T 7/0012; G06T 7/337; G06T 11/005
See application file for complete search history.

(56) References Cited

U.S. PATENT DOCUMENTS 5,982,846 A 11/1999 Toth et al.
6,141,398 A 10/2000 He et al.
(Continued)

FOREIGN PATENT DOCUMENTS

CN 1895174 A 1/2007
CN 102573639 A 7/2012
(Continued)

OTHER PUBLICATIONS

State Intellectual Property Office of the People's Republic of China, Office Action and Search Report Issued in Application No. 201610844028.2, dated Jan. 14, 2019, 9 pages. (Submitted with Partial English Translation).
(Continued)

*Primary Examiner* — David P Porta
*Assistant Examiner* — Shun Lee
(74) *Attorney, Agent, or Firm* — McCoy Russell LLP

(57) ABSTRACT

Provided is a method of selecting a slice configuration of a medical imaging apparatus. According to an example, an expected scanning time for scanning a region of a scanning length by the medical imaging apparatus with each of candidate slice configurations may be determined, and one or more first slice configurations are selected from the candidate slice configurations in a way that the scanning time of each of the first slice configurations is less than a preset threshold. An expected scanning length and an expected redundant scanning dose for scanning the region by the medical imaging apparatus with each of the first slice configurations may be determined. In this way, for scanning the region by the medical imaging apparatus, a target slice configuration may be selected from the first slice configurations according to the expected redundant scanning dose.

17 Claims, 7 Drawing Sheets

(51) Int. Cl.
*G06T 7/33* (2017.01)
*G06T 7/00* (2017.01)
*G06T 11/00* (2006.01)
G06T 7/62 (2017.01)
A61B 5/00 (2006.01)

(52) U.S. Cl.
CPC ............ *G06T 7/0012* (2013.01); *G06T 7/337* (2017.01); *G06T 11/005* (2013.01); *A61B 5/743* (2013.01); *A61B 6/541* (2013.01); *G06T 7/62* (2017.01)

(56) References Cited

U.S. PATENT DOCUMENTS

| | | | | |
|---|---|---|---|---|
| 6,320,929 | B1* | 11/2001 | Von Der Haar | A61B 6/032 378/15 |
| 2004/0179644 | A1* | 9/2004 | Tsuyuki | A61B 6/032 378/8 |
| 2005/0254616 | A1* | 11/2005 | Nakanishi | A61B 6/032 378/4 |
| 2008/0049889 | A1* | 2/2008 | Tsukagoshi | A61B 6/032 378/4 |
| 2012/0213326 | A1* | 8/2012 | Walker | A61B 6/032 378/4 |
| 2015/0265226 | A1* | 9/2015 | Jackson | A61B 6/06 378/16 |
| 2018/0116619 | A1* | 5/2018 | Pang | A61B 6/027 |

FOREIGN PATENT DOCUMENTS

| | | |
|---|---|---|
| CN | 104379059 A | 2/2015 |
| CN | 103494613 B | 10/2015 |
| JP | H11104120 A | 4/1999 |
| JP | 2002102216 A | 4/2002 |
| JP | 2011000134 A | 1/2011 |

OTHER PUBLICATIONS

United States Patent and Trademark Office, Office Action Issued in U.S. Appl. No. 15/799,586, dated Sep. 27, 2019, 12 pages.

* cited by examiner

US 10,687,732 B2

SELECTING SLICE CONFIGURATION OF MEDICAL IMAGING APPARATUS

CROSS REFERENCE TO RELATED APPLICATIONS

This application claims priority to Chinese Patent Application No. 201610844028.2 entitled "METHOD AND DEVICE OF SELECTING SLICE CONFIGURATION" filed on Sep. 22, 2016, the entire contents of which are incorporated herein by reference for all purposes.

BACKGROUND

The present disclosure relates to selecting a slice configuration of a medical imaging apparatus.

In general, a helical retrospective scanning technique may be used when a scan is performed with a medical imaging apparatus (e.g., a CT scanner). To meet a need of image reconstruction, this scanning technique may apply a relatively small scanning pitch. An increase in a number of slices of a detector of a medical imaging apparatus and an increase of a rotational speed of a gantry both make it possible to use a cross-sectional scan manner, which refers to that a scanning bed stays for several seconds at each position to perform scanning and is moved to a next position after a data collection is completed at a current position. This scan manner is referred to as step scan.

Depending on a width of a detector of a current medical imaging apparatus, a scanning length may be a multiple times of the width of the detector of the medical imaging apparatus if a step scan manner is used. When a width n (n is an integer) times that of the detector cannot completely cover a length of a region to be scanned, an actual scanning length may be increased, which will cause the subject to receive an unnecessary X-ray irradiation.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

In general, a medical imaging apparatus sets a slice configuration of a detector according to a region to be scanned of a subject. Under normal circumstances, the slice configuration of the detector of the medical imaging apparatus may include a number of slices and a slice thickness. Different numbers of slices and different slice thicknesses may yield different slice configurations. A width covered by the detector of the medical imaging apparatus at one scan is determined by the slice configuration and the width may be determined by multiplying the number of slices and the slice thickness.

In a step scan manner, when a width n (n is an integer) times that of a detector of a medical imaging apparatus cannot completely cover a length of a region to be scanned of a subject, an actual scanning length may be increased and thus may cause the subject to receive an unnecessary X-ray irradiation. For example, if a length of a region of the subject to be scanned is 50 mm, a number of slices of the slice configuration of the detector of the medical imaging apparatus is 32 and a slice thickness is 0.625 mm, a width that may be covered by the detector of the medical imaging apparatus at one scan is 20 mm (=32×0.625 mm). Therefore, 2.5 (=50/20) steps are to be scanned to have a scanning length of 50 mm scanned. In this case, the detector of the medical imaging apparatus may perform 3 steps of scans, and a total scanning length covered by the detector after 3 steps of scans is 60 mm (=20 mm×3). In this way, there will be 10 mm of scanning length more than the 50 mm to be scanned, resulting in a redundant and excessive scanning of 10 mm, and causing the subject to receive an unnecessary X-ray irradiation of 10 mm.

In view of the above problem, a method and device for selecting a slice configuration of a medical imaging apparatus is provided in the present disclosure, which may effectively reduce or avoid a redundant scanning dose when performing a scan using a medical imaging apparatus. The method and device for selecting a slice configuration of a medical imaging apparatus of the present disclosure will be described in detail with reference to the accompanying drawings. In a case where no conflicts exist, the features of the following examples and implementations may be combined with each other.

Figure 1:
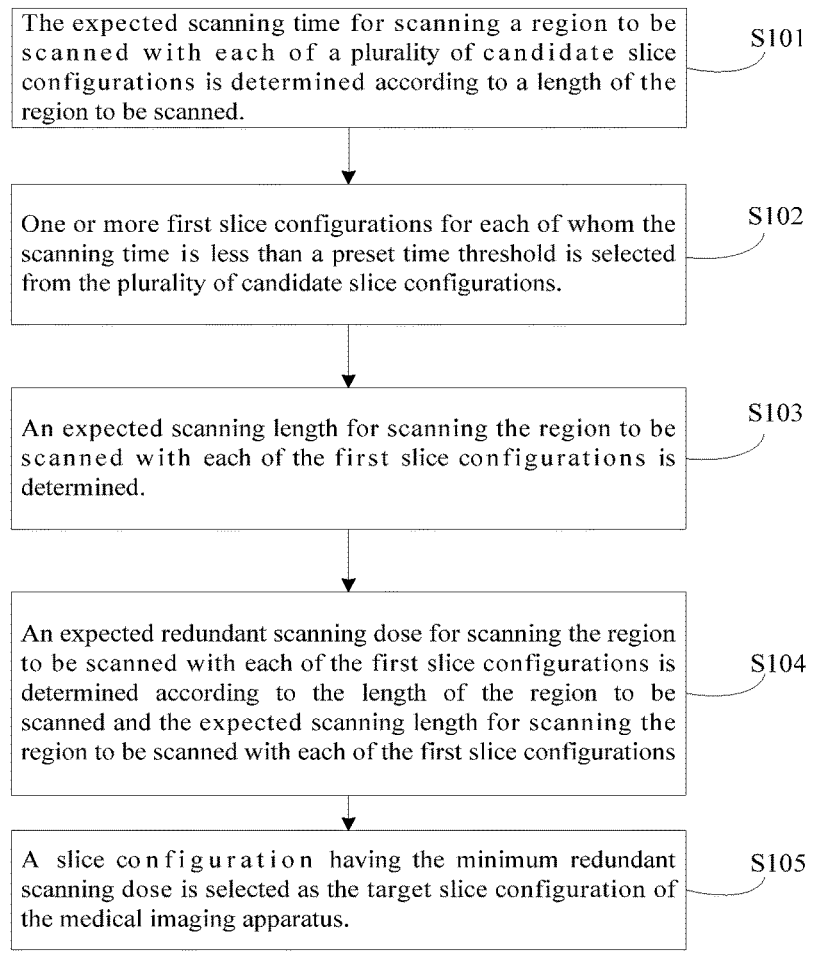
FIG. 1 illustrates a flow chart of a method of selecting a scanning slice configuration of a medical imaging apparatus according to an example of the present disclosure.

FIG. 1 illustrates a flow chart of a method of selecting a slice configuration of a medical imaging apparatus according to an example of the present disclosure. The method includes the following blocks.

At block S101: an expected scanning time for scanning a region of a scanning length with each of a plurality of candidate slice configurations by a medical imaging apparatus is determined, respectively.

At block S102: one or more first slice configurations for each of whom the expected scanning time is less than a preset time threshold are selected by the medical imaging apparatus from the candidate slice configurations.

At block S103: an expected scanning length for scanning the region with each of the first slice configurations is determined, respectively.

At block S104: an expected redundant scanning dose for scanning the region with each of the first slice configurations is determined according to the expected scanning length for scanning the region with each of the first slice configurations and the scanning length of the region to be scanned.

At block S105: a slice configuration having a minimum redundant scanning dose is selected as the target slice configuration of the medical imaging apparatus for scanning.

The method of selecting a slice configuration of a medical imaging apparatus of the present disclosure may ensure that the scanning time of the medical imaging apparatus satisfies application demands by determining the first slice configurations. Then a slice configuration having the minimum redundant scanning dose is selected as a target slice configuration of the medical imaging apparatus for scanning, thus reducing the redundant scanning dose of the medical imaging apparatus under a premise of ensuring the scanning time, thereby effectively reducing the unnecessary X-ray irradiation dose received by the subject.

Figure 2:
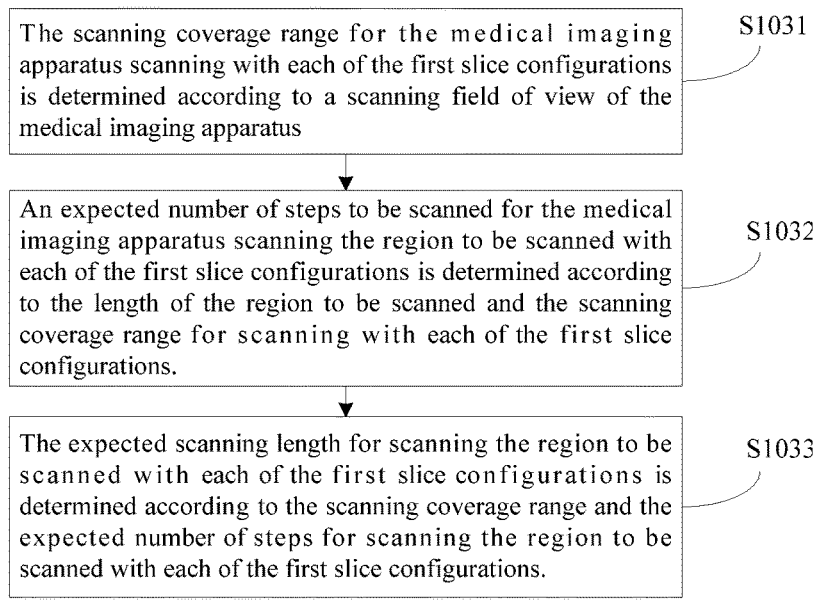
FIG. 2 illustrates a detailed flow chart of block S103 of FIG. 1 according to an example of the present disclosure.

FIG. 2 illustrates a detailed flow chart of block S103 in FIG. 1. The block S103 further includes the following blocks of FIG. 2.

At block S1031: a scanning coverage range for the medical imaging apparatus scanning with each of the first slice configurations may be determined according to a scanning field of view of the medical imaging apparatus.

The scanning field of view indicates a maximum range in the x-y direction of the region to be scanned that may be scanned by the medical imaging apparatus according to a preset slice configuration, and may be determined as the maximum scanning diameter of an X-ray beam which takes the scanning center as the center and penetrates through the slice to reach the region to be scanned. The scanning coverage range indicates a range in the z direction of the region to be scanned in one step of scan, and may be determined according to the scanning field of view. Where, the z direction indicates the forward and backward moving direction of the scanning bed, and the x-y direction indicates a direction orthogonal to the z direction.

At block S1032: an expected number of steps for scanning the region with each of the first slice configurations may be determined according to the scanning coverage range for the medical imaging apparatus scanning with each of the first slice configurations and the scanning length of the region to be scanned.

At block S1033: an expected scanning length for scanning the region to be scanned with each of the first slice configurations may be determined according to the scanning coverage range and the expected number of steps for the medical imaging apparatus scanning the region with each of the first slice configurations.

The calculation formulas involved in each of the above blocks are described below.

(1) At the above block S1031, the calculation formula for determining the scanning coverage range for the medical imaging apparatus scanning with each of the first slice configurations according to the scanning field of view of the medical imaging apparatus may be:

$$fScanDis = \min_{0 \leq \varphi \leq 2\pi} \left( \frac{S \times \left( \frac{\sqrt{R^2 - (fScanFov \times \sin(\varphi))^2}}{(fScanFov \times \cos(\varphi))} - \right) \times (n-1)}{R} \right); \quad (1)$$

where fScanDis represents the scanning coverage range for the medical imaging apparatus scanning with a first slice configuration in which a number of slices is n and a slice thickness is S; fScanFov represents the scanning field of view of the medical imaging apparatus; φ represents a polar angle of an image reconstruction point; and R represents a rotational radius of the detector of the medical imaging apparatus; respectively.

(2) At the above block S1032, the calculation formula for determining the expected number of steps for scanning the region to be scanned with each of the first slice configurations according to the scanning coverage range for the medical imaging apparatus scanning with each of the first slice configurations and the scanning length of the region to be scanned may be:

$$nStepCount = \left\lfloor \frac{sLength}{fScanDis} \right\rfloor + 1; \quad (2)$$

where nStepCount is the expected number of steps for the medical imaging apparatus scanning the region to be scanned with a first slice configuration, sLength is the scanning length of the region to be scanned, and ⌊ ⌋ is a rounding-down operation symbol.

(3) At the above block S1033, the calculation formula for determining the expected scanning length for the medical imaging apparatus scanning the region with each of the first slice configurations according to the scanning coverage range and the expected number of steps for the medical imaging apparatus scanning the region to be scanned with each of the first slice configurations may be:

$$scanLength = nStepCount \times fScanDis; \quad (3)$$

where scanLength is the expected scanning length for the medical imaging apparatus scanning the region to be scanned with a first slice configuration.

(4) At the above block S104, the calculation formula for determining the expected redundant scanning dose for scanning the region to be scanned with each of the first slice configurations according to the expected scanning length for scanning the region with each of the first slice configurations and the scanning length of the region to be scanned may be:

$$RedunData = scanLength - sLength; \quad (4)$$

where RedunData is the expected redundant scanning dose for the medical imaging apparatus scanning the region to be scanned with a first slice configuration.

The expected redundant scanning dose for scanning the region to be scanned with each of the first slice configurations may be determined by the calculation of the above parameters, and then a slice configuration having the minimum redundant scanning dose may be selected as a target slice configuration of the medical imaging apparatus. Specifically, the following two methods may be implemented.

(i) A first method: a slice configuration having a minimum redundant scanning dose is selected from the first slice configurations as the target slice configuration of the medical imaging apparatus to scan all the steps to be scanned. In this case, shorter scanning time and less redundant scanning dose may be ensured.

For example, if a scanning length of a region to be scanned of a subject is 50 mm, and the finally selected target slice configuration includes 30 slices and a slice thickness of 0.6 mm, the scanning coverage range of the target slice configuration is 30×0.6 mm=18 mm, and 2.77 (=50/18) steps are to be scanned for scanning the scanning length of 50 mm, which are rounded to 3 steps. Thus, a total scanning length scanned by the medical imaging apparatus after performing 3 steps of scans with the target slice configuration is 54 mm (=18 mm×3). In this way, there is only 4 mm more than the scanning length of 50 mm, resulting in a redundant scanning dose of 4 mm. Compared with the slice configuration having 32 slices and a slice thickness of 0.625 mm, the redundant scanning dose is reduced by 6 mm.

Figure 3:
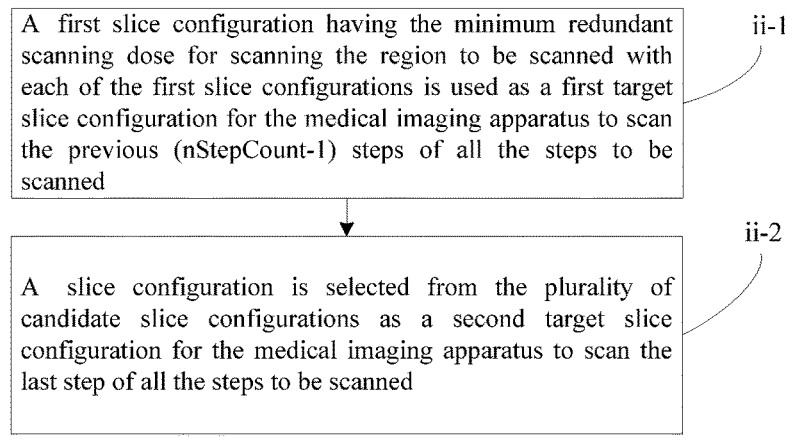
FIG. 3 illustrates a detailed flow chart of block S105 of FIG. 1 according to an example of the present disclosure.
Figure 4:
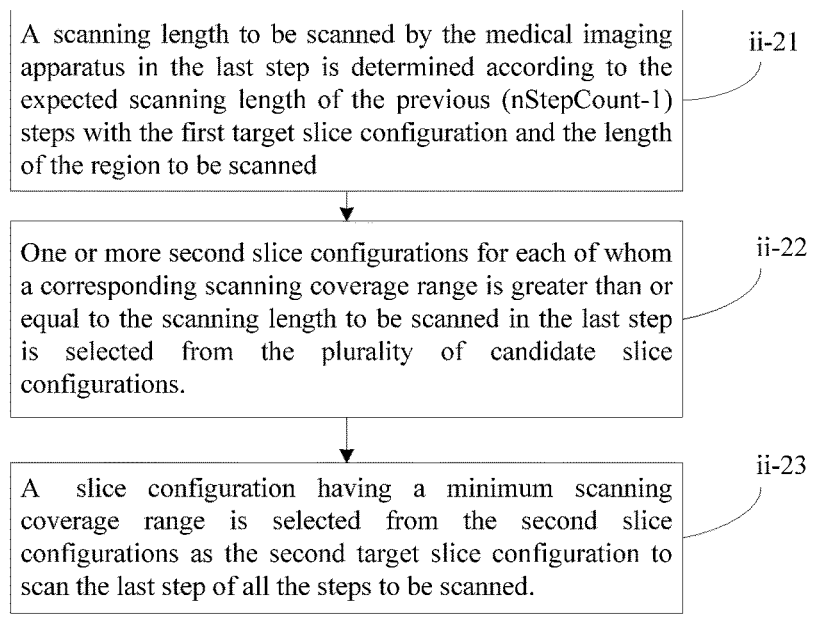
FIG. 4 illustrates a detailed flow chart of block ii-2 of FIG. 3 according to an example of the present disclosure.

(ii) A second method: selecting the target slice configuration of the medical imaging apparatus may include the following blocks to better reduce the redundant scanning dose and save the scanning dose is shown in FIGS. 3 and 4.

At block ii-1 of FIG. 3: a first slice configuration having the minimum redundant scanning dose for scanning the region to be scanned with each of the first slice configurations is used as a first target slice configuration for the medical imaging apparatus to scan the previous (nStepCount-1) steps of all the steps to be scanned; and At block ii-2 of FIG. 3: a slice configuration is selected from the plurality of candidate slice configurations as a second target slice configuration for the medical imaging apparatus to scan the last step of all the steps to be scanned so that the redundant scanning dose is minimized or there is no redundant scanning dose.

In particular, the block ii-2 may specifically include the following blocks.

At block ii-21 of FIG. 4: a scanning length to be scanned by the medical imaging apparatus in the last step is determined according to the expected scanning length of the previous (nStepCount-1) steps with the first target slice configuration and the length of the region to be scanned.

At block ii-22 of FIG. 4: one or more second slice configurations for each of whom a corresponding scanning coverage range is greater than or equal to the scanning length to be scanned in the last step is selected from the plurality of candidate slice configurations.

At block ii-23: a slice configuration having a minimum scanning coverage range is selected from the second slice configurations as the second target slice configuration to scan the last step of all the steps to be scanned.

The calculation formulas involved in each of the above blocks are described below.

At the above block ii-21, the calculation formula for determining the scanning length to be scanned by the medical imaging apparatus in the last step according to the expected scanning length of the previous (nStepCount-1) steps with the first target slice configuration and the length of the region to be scanned may be:

$$sLength_{Last} = sLength - \left\lfloor \frac{sLength}{fScanDis_{MinRedun}} \right\rfloor \times fScanDis_{MinRedun} \quad (5)$$

where $fScanDis_{MinRedun}$ is the scanning coverage range for the medical imaging apparatus scanning with the first target slice configuration; and $sLength_{Last}$ is the scanning length to be scanned by the medical imaging apparatus in the last step.

For example, if the scanning length of the region to be scanned of the subject is 50 mm, and the finally selected first target slice configuration includes 30 slices and a slice thickness of 0.6 mm, the scanning coverage range for the medical imaging apparatus scanning with the first target slice configuration is 18 mm (=30×0.6 mm), and 2.77 (=50/18) steps are to be scanned for scanning the scanning length of 50 mm, which is rounded to 3 steps.

When the slice configuration having 30 slices and a slice thickness of 0.6 mm is used for scanning the first 2 steps by the medical imaging apparatus, a total scanning length of the previous 2 steps is 36 mm (=18 mm×2), and the scanning length to be scanned in the remaining last step is 14 mm (=50 mm−36 mm).

Then, one or more second slice configurations for each of whom the corresponding scanning coverage range is greater than or equal to 14 mm are selected from the plurality of candidate slice configurations. For example, the second slice configurations may include 32 slices*0.5 mm (the scanning coverage range is 16 mm), 25 slices*0.6 mm (the scanning coverage range is 15 mm), 28 slices*0.5 mm (the scanning coverage range is 14 mm), and so on.

Finally, a second slice configuration having the minimum scanning coverage range, i.e. a second slice configuration of 28 slices*0.5 mm (the scanning coverage range is 14 mm) is selected from the above second slice configurations as the second target slice configuration to be used by the medical imaging apparatus for scanning the last step. At this time, the scanning coverage range of the detector of the medical imaging apparatus is exactly equal to the scanning length to be scanned in the last step so that the redundant scanning dose may be reduced to zero. However, if there is no second slice configuration of 28 slices*0.5 mm (the scanning coverage range is 14 mm) in the second slice configurations, then the second slice configuration of 25 slices*0.6 mm (the scanning coverage range is 15 mm) may be selected to scan the last step so that the expected redundant scanning dose is reduced to 1 mm. Therefore, the method has achieved less redundant scanning dose than the first method.

Of course, under the premise that the scanning time satisfies the conditions described herein, slice configurations having less redundant scanning dose may also be selected, and then the slice configuration having the shortest scanning time is selected therefrom. The specific selecting manner should depend on a region to be scanned.

In some embodiments, the method disclosed in the present disclosure may be used for scanning a heart. The heart may be regarded as a relatively special region to be scanned. During a scanning process, due to the continuous beat of the heart, the medical imaging apparatus (e.g., a CT scanner) is configured to collect data in a phase of a relatively smaller heart movement (e.g., diastolic phase or systolic phase). Additionally, there may be an inconsistency among heart beats. This inconsistency may result in that time resolutions of images of different locations are inconsistent, and therefore a relatively higher demand is made for the scanning speed so as to complete a scan in a shortest time. This calls for a combination of the ECG (electrocardiogram) signal of a patient and a method of selecting a slice configuration of a medical imaging apparatus of the present disclosure to ensure a minimum redundant scanning dose and a fastest scanning speed.

A method of selecting a slice configuration of a medical imaging apparatus of the present disclosure will be described below with the region to be scanned as a heart.

Usually, a step scan manner may be used when a heart is to be scanned, that is, a scanning bed is moved to a next position once a scan is completed at a current position, and a time to start a scan is then decided according to the ECG (electrocardiogram) signal. It may be seen from the ECG that in some RR intervals (the RR interval is used to calculate a ventricular rate, and refers to the time between R waves in two QRS waves, i.e. refers to an interval of R wave peaks in two adjacent heartbeats in the electrocardiogram, which reflects the interval between two heartbeats), a scan is not to be started until a specified phase position of a next RR interval is reached since a phase in which data are to be collected is missed during the current RR interval when the scanning bed is in place, resulting in a longer entire scanning time. However, due to a physiological characteristic of the heart, the scanning time of the heart may be as short as possible. Therefore, a slice configuration may be based on a heart rate, a forward distance and forward speed of each scan, etc. to ensure a fastest scanning speed and a least redundant scanning dose.

Figure 5:
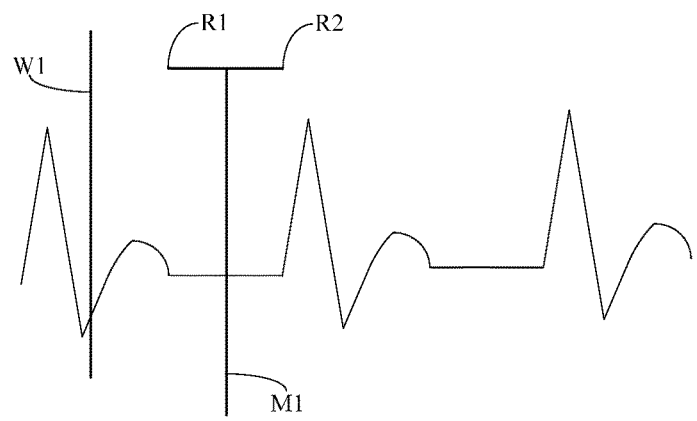
FIG. 5 illustrates a schematic diagram of an electrocardiogram according to an example of the present disclosure.

For example, FIG. 5 illustrates a schematic diagram of an electrocardiogram according to an example of the present disclosure. In the electrocardiogram shown in FIG. 5, if a corresponding phase position W1 when the scanning bed is in place is before an x-ray exposure start phase position R1 of the current RR interval, data may be collected from the x-ray exposure start phase position R1 of the current RR interval. The latest collection phase position of the data collection is at an x-ray exposure end phase position R2 of the current RR interval. The data may be collected in a data collection area formed by the x-ray exposure start phase position R1 of the current RR interval and the x-ray exposure end phase position R2 of the current RR interval. For example, as shown in FIG. 5, the data is collected at a data collection area with a phase position M1 as the centre.

Figure 6:
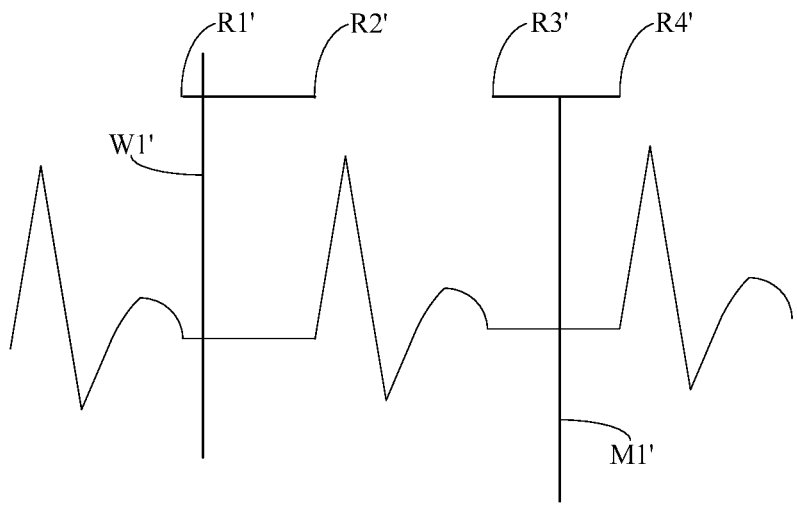
FIG. 6 illustrates a schematic diagram of another electrocardiogram according to an example of the present disclosure.

FIG. 6 illustrates a schematic diagram of another electrocardiogram according to an example of the present disclosure. In the electrocardiogram shown in FIG. 6, if a corresponding phase position W1' when the scanning bed is in place is behind an x-ray exposure start phase position R1' of the current RR interval, the data may be collected only at an x-ray exposure start phase position R3' of the next RR interval behind an x-ray exposure end phase position R2' of the current RR interval. The latest collection phase position of the data collection is at an x-ray exposure end phase position R4' of the next RR interval. The data may be collected in a data collection area formed by the x-ray exposure start phase position R3' of the next RR interval and the x-ray exposure end phase position R4' of the next RR interval. As shown in FIG. 6, the data is collected at a data collection area with a phase position M1' as the centre.

Considering the particularity of a heart scan, when the region to be scanned is a heart, a method of selecting a slice configuration of a medical imaging apparatus of the present disclosure is as follows.

At the above block S101 of FIG. 1, determining an expected scanning time for a medical imaging apparatus scanning a region to be scanned with each of a plurality of candidate slice configurations may further include: determining maximum and minimum values of the expected scanning time for the medical imaging apparatus scanning a heart to be scanned with each of the candidate slice configurations according to the length of the heart to be scanned and the electrocardiogram of the heart to be scanned.

At the above block S102 of FIG. 1, selecting one or more first slice configurations for each of whom the corresponding scanning time is less than a preset time threshold from the plurality of candidate slice configurations may include: selecting one or more first slice configurations for each of whom the corresponding maximum value of the scanning time is less than the preset time threshold from the plurality of candidate slice configurations.

Figure 7:
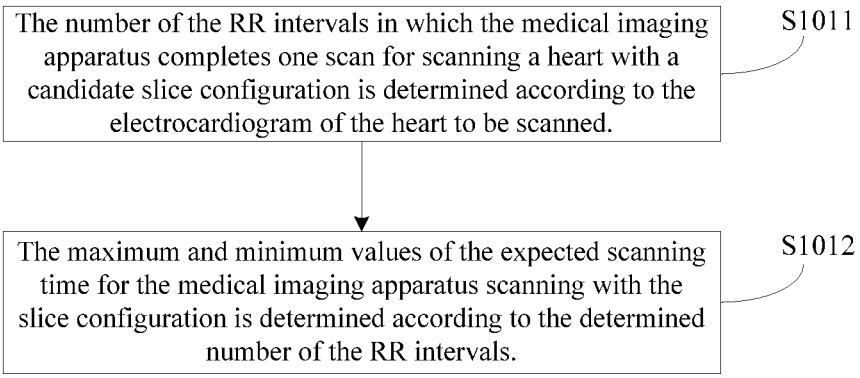
FIG. 7 illustrates a detailed flow chart of block S101 of FIG. 1 when a region to be scanned is a heart according to an example of the present disclosure.
Figure 8:
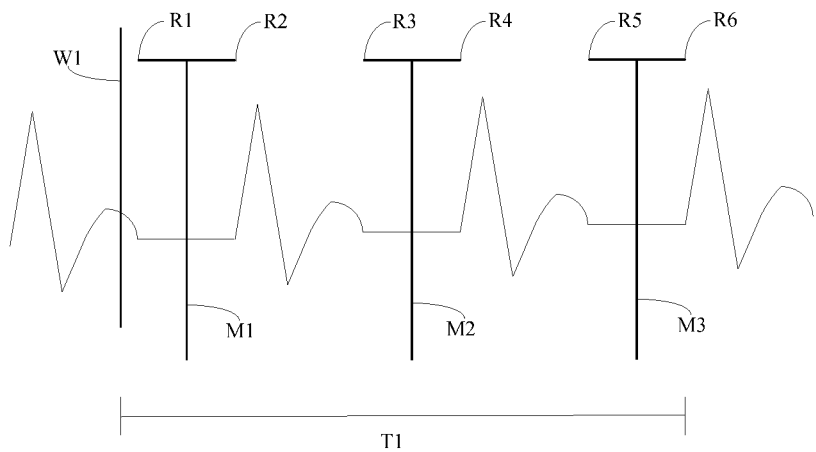
FIGS. 8, 9, 10, and 11 illustrate schematic diagrams of four electrocardiograms showing expected scanning time and RR intervals according to examples of the present disclosure.
Figure 9:
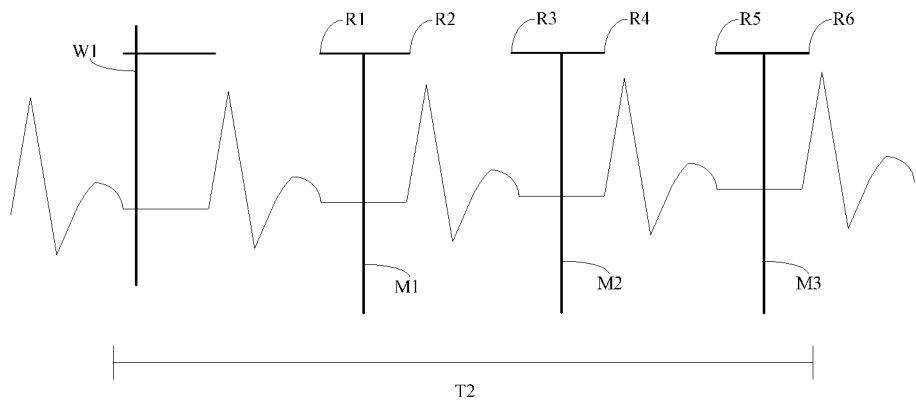
Figure 10:
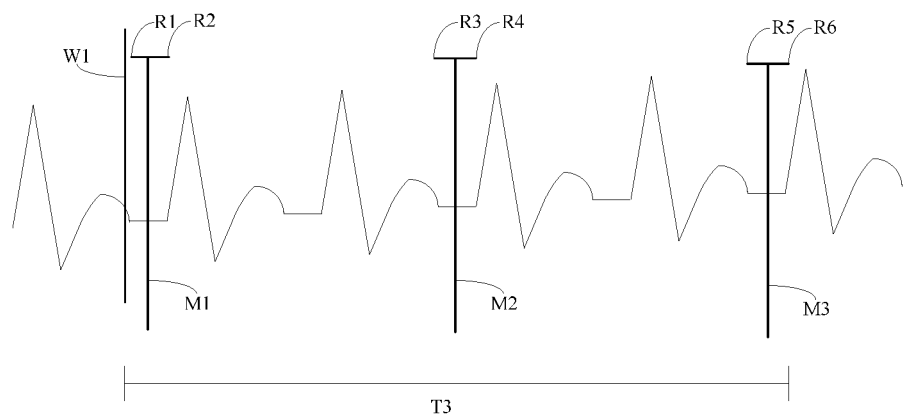
Figure 11:
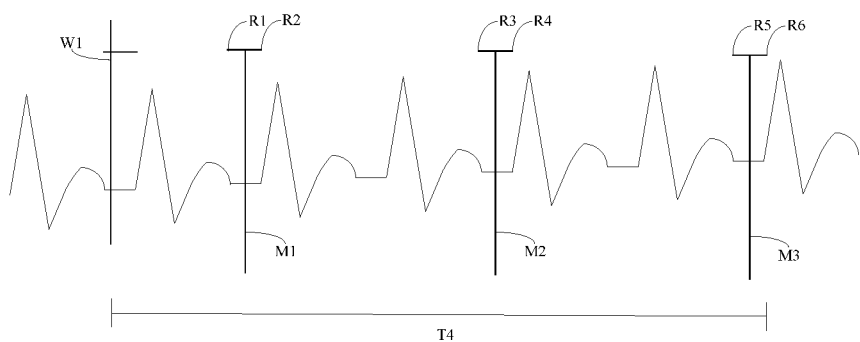

Specifically, FIG. 7 illustrates a detailed flow chart of block S101 of FIG. 1 when a region to be scanned is a heart. At the above block S101 of FIG. 1, determining the maximum and minimum values of the expected scanning time for the medical imaging apparatus scanning the heart to be scanned with each of the plurality of candidate slice configurations according to the length of the heart to be scanned and the electrocardiogram of the heart to be scanned includes the following blocks.

At block S1011: a number of RR intervals in which the medical imaging apparatus completes one scan for scanning the heart to be scanned with each of candidate slice configurations may be determined according to the electrocardiogram of the heart to be scanned; the number of RR intervals may be counted directly from the electrocardiogram; and At block S1012: the maximum and minimum values of the expected scanning time for the medical imaging apparatus scanning the heart to be scanned with each of the candidate slice configurations are determined according to the determined number of RR intervals.

The calculation formulas involved in each of the above blocks are described below.

At the above block S1012, the calculation formula for determining the maximum value of the scanning time for the medical imaging apparatus scanning the heart to be scanned with a candidate slice configuration may be:

$$\text{scanTime}_{max} = n\text{StepCount}_i \times RR\text{Interval} \times RR\text{Count} + T \quad (6)$$

The calculation formula for determining the minimum value of the scanning time for the medical imaging apparatus scanning the heart to be scanned with a candidate slice configuration may be:

$$\text{scanTime}_{min} = n\text{StepCount}_i \times RR\text{Interval} \times RR\text{Count} - RR\text{Interval} + T \quad (7)$$

where $\text{scanTime}_{max}$ is the maximum value of the scanning time for the medical imaging apparatus scanning the heart to be scanned with a candidate slice configuration; $\text{scanTime}_{min}$ is the minimum value of the scanning time for the medical imaging apparatus scanning the heart to be scanned with the candidate slice configuration; $n\text{StepCount}_i$ is the expected number of steps for the medical imaging apparatus scanning the heart to be scanned with the candidate slice configuration; RRInterval is the RR interval of the heart to be scanned displayed on the electrocardiogram; RRCount is the number of RR intervals in which the medical imaging apparatus completes one scan for scanning the heart to be scanned with the candidate slice configuration; and T is data collection time of the medical imaging apparatus.

Specifically, a time left for a scanning bed to move in a RR interval is a difference between the RR interval and the data collection time of the medical imaging apparatus (RRInterval-T), If $(RRInterval-T)*V > fMoveDis$, $RRCount=1$ (8)

If $(RRInterval-T)*V \leq fMoveDis$, $RRCount=2$ (9)

where V is a moving speed of the scanning bed and fMoveDis is the forward distance of the scanning bed (equivalent to the scanning coverage range of the medical imaging apparatus when scanning with a candidate slice configuration). If $(RRInterval-T)*V > fMoveDis$, it may indicate that both the data collection and the bed movement may be completed in one RR interval, and RRCount=1. Otherwise it may indicate that both the data collection and the bed movement cannot be completed during a single RR interval but are to be completed in two RR intervals. For example, a RR interval is only used for the movement of a bed, while the other RR interval is only used for performing scanning to collect data, and RRCount=2. The data collection time is determined by a scanning speed, and the scanning speed is determined by the rotational speed of the medical imaging apparatus. The scanning speed is generally ⅔ of the rotational speed of the medical imaging apparatus.

FIGS. 8, 9, 10, and 11 illustrate time for completing scanning of a same number of steps (e.g., 3 steps) for a heart when the scanning bed is in place and the corresponding RR interval phase positions of the heart are different according to examples of the present disclosure.

(1) One data collection may be completed in one RR interval, and a corresponding phase position is before an x-ray exposure start phase position of a current RR interval when the scanning bed is in place. In this case, the minimum value of the scanning time is as shown by T1 in FIG. 8.

(2) One data collection may be completed in one RR interval, and the corresponding phase position is after the x-ray exposure start phase position of the current RR interval when the scanning bed is in place. In this case, the maximum value of the scanning time is as shown by T2 in FIG. 9.

(3) One data collection may be completed in two RR intervals, and the corresponding phase position is before the x-ray exposure start phase position of the current RR interval when the scanning bed is in place. In this case, the minimum value of the scanning time is as shown by T3 in FIG. 10.

(4) One data collection may be completed in two RR intervals, and the corresponding phase position is after the x-ray exposure start phase position of the current RR interval when the scanning bed is in place. In this case, the maximum value of the scanning time is as shown by T4 in FIG. 11.

In FIGS. 8, 9, 10, and 11, W1 represents the corresponding phase position when the scanning bed is in place, R1 and R2 represent an x-ray exposure start phase position and an x-ray exposure end phase position of a first data collection area, R3 and R4 represent an x-ray exposure start phase position and an x-ray exposure end phase position of a second data collection area, R5 and R6 represent the an x-ray exposure phase position and an x-ray exposure end phase position of a third data collection area, M1 represents a data collection at a centre phase position of the first data collection area, M2 represents a data collection at a centre phase position of the second data collection area, and M3 represents a data collection at a centre phase position of the third data collection area.

When a width n (n is an integer) times that of the scanning coverage range of the medical imaging apparatus cannot completely cover the scanning length of the region to be scanned, a slice configuration actually used by the medical imaging apparatus may be determined according to the length of the region to be scanned and the method of selecting the slice configuration described above. If the method of selecting the slice configuration described above is used, the redundant scanning dose of the medical imaging apparatus may be reduced under the premise of ensuring the scanning time, thereby effectively reducing the unnecessary scanning irradiation dose received by the subject.

Figure 12:
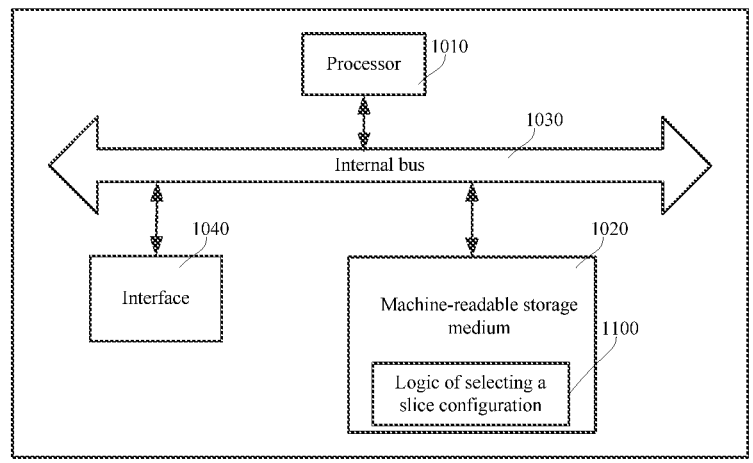
FIG. 12 illustrates a schematic diagram of a hardware structure of a medical imaging apparatus according to an example of the present disclosure.

In addition, FIG. 12 illustrates a schematic diagram of a hardware structure of a medical imaging apparatus according to an example of the present disclosure. As shown in FIG. 12, the apparatus includes a processor 1010 and a machine-readable storage medium 1020, where the processor 1010 and the machine-readable storage medium 1020 are typically interconnected by means of an internal bus 1030. In other possible implementations, the apparatus may also include an external interface 1040 to enable communication with other apparatuses or components.

In different examples, the machine-readable storage medium 1020 may be a Read-Only Memory (ROM), a volatile memory, a non-volatile memory, a flash memory, a storage drive (e.g., a hard disk drive), a solid hard disk, any type of storage disks (such as a compact disc, a DVD, etc.), or a similar storage medium, or a combination thereof.

Figure 13:
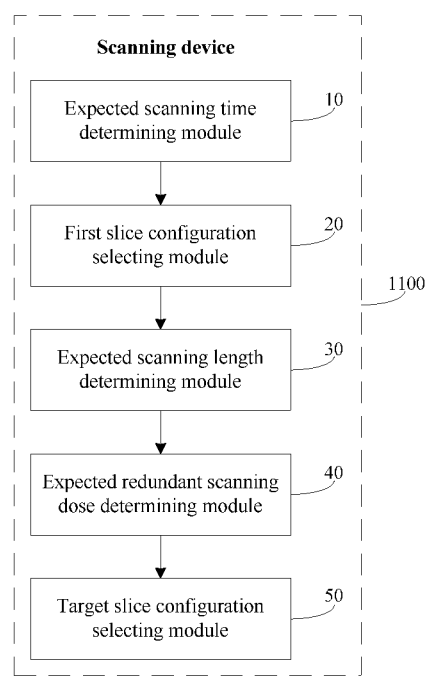
FIG. 13 illustrates a functional block diagram of logic of selecting a slice configuration according to an example of the present disclosure.

Further, the machine-readable storage medium 1020 stores machine-executable instructions corresponding to logic 1100 of selecting a slice configuration. According to functions, as shown in FIG. 13, the logic 1100 of selecting a slice configuration may include:

an expected scanning time determining module 10 configured to determine an expected scanning time for scanning a region of a scanning length to be scanned with each of a plurality of candidate slice configurations, respectively;

a first slice configuration selecting module 20 configured to select one or more first slice configurations for each of whom a corresponding scanning time is less than a preset time threshold from the plurality of candidate slice configurations;

an expected scanning length determining module 30 configured to determine an expected scanning length for scanning the region to be scanned with each of the first slice configurations according to a scanning coverage range for scanning the region to be scanned with each of the first slice configurations and the length of the region to be scanned;

an expected redundant scanning dose determining module 40 configured to determine an expected redundant scanning dose for scanning the region to be scanned with each of the first slice configurations according to the expected scanning length for scanning the region to be scanned with each of the first slice configurations and the length of the region to be scanned; and a target slice configuration selecting module 50 configured to select a slice configuration having the minimum redundant scanning dose as a target slice configuration of the medical imaging apparatus.

In a scanning device of the present disclosure, the first slice configuration determining module may ensure that the scanning time satisfies conditions disclosed herein, and the target slice configuration selecting module may select a slice configuration having the minimum redundant scanning dose as a target slice configuration of the medical imaging apparatus for scanning, thus reducing the redundant scanning dose of the medical imaging apparatus under the premise of ensuring the scanning time, thereby effectively reducing the unnecessary scanning irradiation dose received by the subject.

Figure 14:
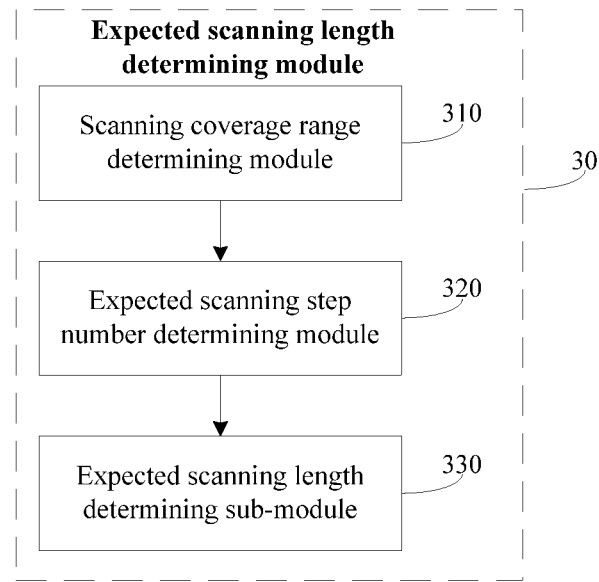
FIG. 14 illustrates a block diagram of a structure of an expected scanning length determining module of FIG. 13 according to an example of the present disclosure.

Specifically, FIG. 14 illustrates a block diagram of a structure of an expected scanning length determining module of FIG. 13 according to an example of the present disclosure. The expected scanning length determining module 30 includes:

a scanning coverage range determining module 310 configured to determine a scanning coverage range for the medical imaging apparatus scanning with each of the first slice configurations according to a scanning field of view of the medical imaging apparatus;

an expected scanning step number determining module 320, connected with the scanning coverage range determining module 310 and configured to determine the expected number of steps for scanning the region to be scanned with each of the first slice configurations according to the scanning coverage range for the medical imaging apparatus scanning with each of the first slice configurations and the length of the region to be scanned; and an expected scanning length determining sub-module 330, connected with the scanning coverage range determining module 310 and the expected scanning step number determining module 320 and configured to determine the expected scanning length for scanning the region to be scanned with each of the first slice configurations according to the scanning coverage range and the expected number of steps for scanning the region to be scanned with each of the first slice configurations.

It is to be particularly noted that the target slice configuration selecting module 50 of the scanning device of the present disclosure corresponds to the method of selecting a slice configuration of the medical imaging apparatus of the present disclosure described above, and the following two methods may also be used in the process of selecting a slice configuration of a medical imaging apparatus.

Figure 15:
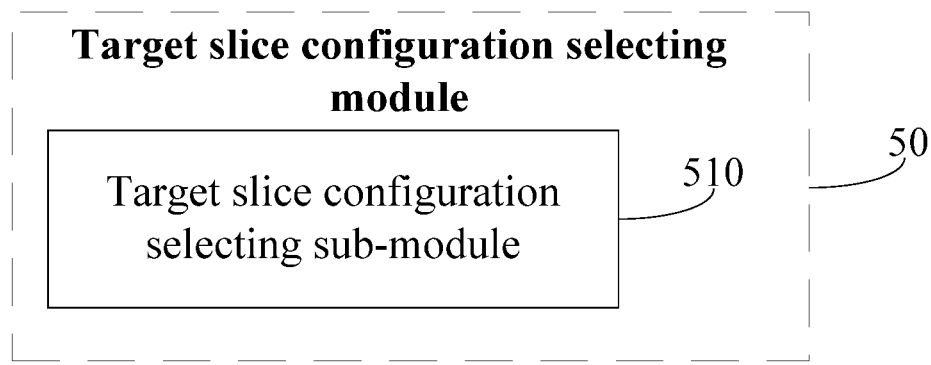
FIG. 15 illustrates a block diagram of a structure of a slice configuration selecting module of FIG. 13 according to an example of the present disclosure.

(i) Corresponding to the first method i described in the method of selecting a target slice configuration of the medical imaging apparatus of the present disclosure described above, the selected slice configuration having the minimum redundant scanning dose is referred to as the target slice configuration. In the first case, FIG. 15 illustrates a block diagram of a structure of a target slice configuration selecting module of FIG. 13 according to an example of the present disclosure. The target slice configuration selecting module 50 includes a target slice configuration selecting sub-module 510 configured to select a first slice configuration of the minimum redundant dose as a target slice configuration for the medical imaging apparatus to scan all the steps to be scanned.

Figure 16:
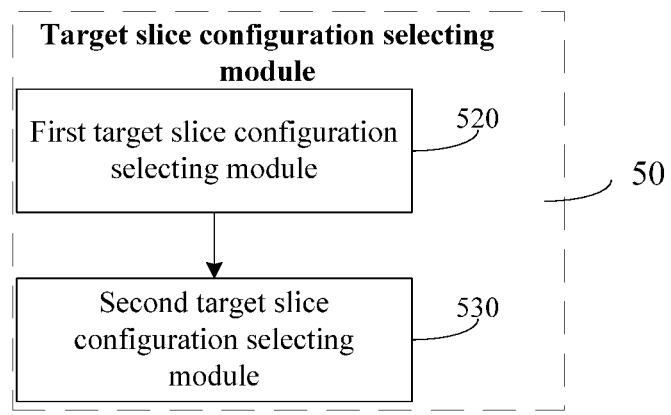
FIG. 16 illustrates a block diagram of another structure of a slice configuration selecting module of FIG. 13 according to an example of the present disclosure.

(ii) Corresponding to the second method ii, of FIGS. 3 and 4, described in the method of selecting a slice configuration of the present disclosure described above, the selected first slice configuration having the minimum redundant scanning dose is referred to as the first target slice configuration and the selected slice configuration selected from a plurality of candidate slice configurations and having the minimum redundant scanning dose is referred to as the second target slice configuration. In the second case, FIG. 16 illustrates a block diagram of another structure of a logic of selecting a target slice configuration of FIG. 13 according to an example of the present disclosure. The target slice configuration selecting module 50 includes:

a first target slice configuration selecting module 520 configured to select a first slice configuration of the minimum redundant dose as a first target slice configuration for the medical imaging apparatus to scan the previous (nStepCount-1) steps of all the steps to be scanned;

a second target slice configuration selecting module 530 configured to select a slice configuration having a minimum scanning coverage range as a second target slice configuration for the medical imaging apparatus to scan the last step of all the steps to be scanned.

Figure 17:
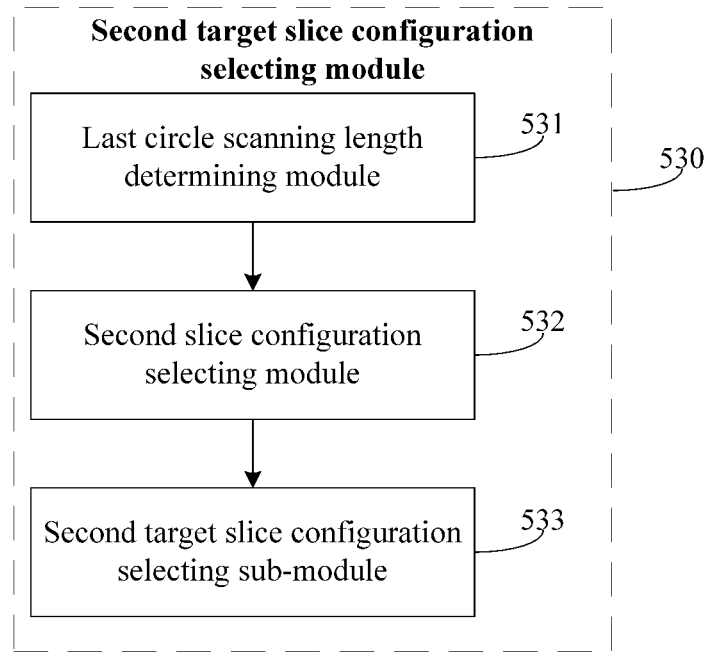
FIG. 17 illustrates a block diagram of a structure of a last step slice configuration selecting module of FIG. 13 according to an example of the present disclosure.

FIG. 17 illustrates a block diagram of a structure of the second target slice configuration selecting module of FIG. 13 according to an example of the present disclosure. Further, the second target slice configuration selecting module 530 includes:

a last step scanning length determining module 531 configured to determine the scanning length to be scanned in the last step by the medical imaging apparatus according to the scanning length of the previous (nStepCount-1) steps for the medical imaging apparatus scanning the region to be scanned with the first target slice configuration and the length of the region to be scanned; and a second slice configuration determining module 532, connected with the last step scanning length determining module 531 and configured to select one or more second slice configurations for each of whom the corresponding scanning coverage range is greater than or equal to the scanning length to be scanned in the last step from the plurality of candidate slice configurations.

a second target slice configuration selecting sub-module 533 connected with the last step scanning length determining module 531 and the second slice configuration determining module 532 and configured to select a slice configuration having the minimum scanning coverage range from the second slice configurations as the second target slice configuration.

Corresponding to a method of selecting a slice configuration of a medical imaging apparatus of the present disclosure described above, when a heart is scanned, in the scanning device of the present disclosure:

the expected scanning time determining module 10 determines maximum and minimum values of the corresponding scanning time for the medical imaging apparatus scanning the heart to be scanned with each of the candidate slice configurations according to the scanning length of the heart to be scanned and the electrocardiogram of the heart to be scanned; and the first slice configuration determining module 20 selects one or more first slice configurations for each of whom the maximum value of the scanning time is less than the preset time threshold from the plurality of candidate slice configurations.

Figure 18:
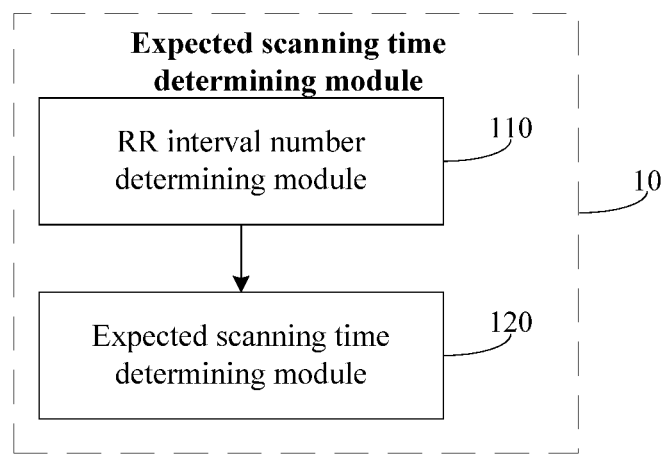
FIG. 18 illustrates a block diagram of a structure of an expected scanning time determining module of FIG. 13 according to an example of the present disclosure.

Specifically, FIG. 18 illustrates a block diagram of a structure of a scanning time determining module of FIG. 13 according to an example of the present disclosure. The scanning time determining module 10 includes:

an RR interval number determining module 110 configured to determine a number of RR intervals in which the medical imaging apparatus completes one scan for scanning the heart to be scanned with an candidate slice configuration according to the electrocardiogram of the heart to be scanned; and a scanning time determining module 120, connected with the RR interval number determining module 110 and configured to determine maximum and minimum values of the scanning time for the medical imaging apparatus scanning the heart to be scanned with the candidate slice configuration according to the determined number of RR intervals.

Since the calculation formulas involved in the respective modules of the scanning device of the present disclosure described above have been described in detail in the example of the method of selecting a slice configuration of the medical imaging apparatus of the present disclosure described above, the description thereof will not be repeated here.

With software implementation as an example, further descriptions are made below on how a medical imaging apparatus performs the logic 1100 of selecting a slice configuration. In this example, the logic 1100 of selecting a slice configuration of the present disclosure is to be understood as computer-executable instructions stored in the machine-readable storage medium 1020. When the processor 1010 on the medical imaging apparatus of the present disclosure executes the logic 1100 of selecting a slice configuration, the processor 1010 may be caused to perform the following operations by invoking the instructions corresponding to the logic 1100 of selecting a slice configuration stored on the machine-readable storage medium 1020:

determining an expected scanning time for scanning the region to be scanned with each of a plurality of candidate slice configurations;

selecting one or more first slice configurations for each of whom the expected scanning time is less than a preset time threshold from the plurality of candidate slice configurations;

determining an expected scanning length for scanning the region to be scanned with each of the first slice configurations according to the scanning coverage range for scanning with each of the first slice configurations and the length of the region to be scanned;

determining an expected redundant scanning dose for scanning the region to be scanned with each of the first slice configurations according to the expected scanning length for scanning the region to be scanned with each of the first slice configurations and the length of the region to be scanned; and selecting a slice configuration having the minimum redundant scanning dose as a target slice configuration of the medical imaging apparatus.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above. Without departing from the scope of the technical scheme of the present disclosure, any simple alterations, equal changes and modifications made based on technical essences of the present disclosure should fall within the protection scope of the technical scheme of the present disclosure.

For simplicity and illustrative purposes, the present disclosure is described by referring mainly to examples thereof. In the above descriptions, numerous specific details are set forth to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The invention claimed is:

1. A method of selecting a slice configuration, comprising:
when a region to be scanned is a heart, determining, by a medical imaging apparatus, maximum and minimum values of scanning time for scanning the heart by the medical imaging apparatus with each of a plurality of candidate slice configurations according to a length of the heart and an electrocardiogram of the heart;
selecting, by the medical imaging apparatus, one or more first slice configurations for each of whom the maximum value of the scanning time is less than a preset time threshold from the plurality of candidate slice configurations;
determining, by the medical imaging apparatus, an expected scanning length for scanning the region with each of the first slice configurations;
determining, by the medical imaging apparatus, an expected redundant scanning dose for scanning the region with each of the first slice configurations according to the expected scanning length for scanning the region with each of the first slice configurations and a scanning length of the region; and
selecting, by the medical imaging apparatus, a target slice configuration according to the redundant scanning dose for scanning the region with each of the first slice configurations, wherein the region is to be scanned by the medical imaging apparatus with the target slice configurations;
wherein determining the maximum and minimum values of the scanning time for scanning the heart with each of the plurality of candidate slice configurations according to the length of the heart and the electrocardiogram of the heart comprises:
for each of the plurality of candidate slice configurations,
determining, by the medical imaging apparatus, a number of RR intervals in which the medical imaging apparatus completes one scan with the candidate slice configuration according to the electrocardiogram of the heart;
determining, by the medical imaging apparatus, an expected number of steps according to a scanning coverage range for the medical imaging apparatus scanning with the candidate slice configuration and the length of the heart;
determining, by the medical imaging apparatus, a RR interval of the heart displayed on the electrocardiogram; and
determining, by the medical imaging apparatus, the maximum and minimum values of the scanning time for scanning the heart with the candidate slice configuration according to the determined number of RR intervals, the expected number of steps, and the RR interval of the heart.

2. The method of claim 1, wherein determining the expected scanning length for scanning the region with one of the first slice configurations comprises:
determining, by the medical imaging apparatus, a scanning coverage range for the medical imaging apparatus scanning with the first slice configuration according to a scanning field of view of the medical imaging apparatus;

determining, by the medical imaging apparatus, an expected number of steps for scanning the region with the first slice configuration according to the scanning coverage range for the medical imaging apparatus scanning with the first slice configuration and the scanning length of the region; and determining, by the medical imaging apparatus, the expected scanning length for scanning the region with the first slice configuration according to the scanning coverage range and the expected number of steps for the medical imaging apparatus scanning the region with the first slice configuration.

3. The method of claim 2, wherein determining the scanning coverage range for the medical imaging apparatus scanning with the first slice configuration according to the scanning field of view of the medical imaging apparatus comprises:

calculating, by the medical imaging apparatus, the scanning coverage range for the medical imaging apparatus scanning with the first slice configuration based on the following formula, $$fScanDis = \min_{0 \leq \varphi \leq 2\pi}\left( \frac{S \times \left( \frac{\sqrt{R^2 - (fScanFov \times \sin(\varphi))^2} - (fScanFov \times \cos(\varphi))}{} \right) \times (n-1)}{R} \right);$$

wherein:
fScanDis represents the scanning coverage range for the medical imaging apparatus scanning with the first slice configuration in which a number of slices is n and a slice thickness is S;
fScanFov represents the scanning field of view of the medical imaging apparatus;
φ represents a polar angle of an image reconstruction point; and
R represents a rotational radius of the medical imaging apparatus.

4. The method of claim 2, wherein determining the expected number of steps for scanning the region with the first slice configuration comprises:

performing, by the medical imaging apparatus, a rounding-down operation on a quotient of the scanning length of the region to be scanned and the scanning coverage range for the medical imaging apparatus scanning with the first slice configuration to obtain an integer result, and adding, by the medical imaging apparatus, one to the obtained integer result to obtain the expected number of steps for scanning the region with the first slice configuration.

5. The method of claim 2, wherein determining the expected scanning length for scanning the region with the first slice configuration comprises:

multiplying, by the medical imaging apparatus, the expected number of steps for scanning the region with the first slice configuration and the scanning coverage range for the medical imaging apparatus scanning with the first slice configuration to obtain the expected scanning length for scanning the region by the medical imaging apparatus with the first slice configuration.

6. The method of claim 1, wherein determining the expected redundant scanning dose for scanning the region with the first slice configuration comprises:

subtracting, by the medical imaging apparatus, the expected scanning length for scanning the region with the first slice configuration from the scanning length of the region to obtain the expected redundant scanning dose of the medical imaging apparatus for scanning the region with the first slice configuration.

7. The method of claim 1, wherein selecting a target slice configuration according to the expected redundant scanning dose comprises:

selecting, by the medical imaging apparatus, a slice configuration having a minimum expected redundant scanning dose from the first slice configurations as the target slice configuration to scan all the expected steps to be scanned.

8. The method of claim 1, wherein selecting a target slice configuration according to the expected redundant scanning dose comprises:

selecting, by the medical imaging apparatus, a first slice configuration having a minimum expected redundant scanning dose from the first slice configurations as a first target slice configuration to scan previous (nStepCount-1) steps of all the expected number of steps nStepCount to be scanned; and selecting, by the medical imaging apparatus, a second target slice configuration from the plurality of candidate slice configurations to scan a last step of all the expected number of steps nStepCount to be scanned.

9. The method of claim 8, wherein selecting the second target slice configuration from the plurality of candidate slice configurations comprises:

determining, by the medical imaging apparatus, an expected scanning length to be scanned in the last step according to an expected scanning length of the previous (nStepCount-1) steps for scanning with the first target slice configuration and the scanning length of the region;

selecting, by the medical imaging apparatus, one or more second slice configurations from the plurality of candidate slice configurations, wherein the scanning coverage range of each of the second slice configurations is greater than or equal to the expected scanning length to be scanned in the last step; and selecting, by the medical imaging apparatus, a second slice configuration having a minimum scanning coverage range from the second slice configurations as the second target slice configuration to scan the last step.

10. The method of claim 1, wherein determining the number of RR intervals in which the medical imaging apparatus completes one scan with the candidate slice configuration according to the electrocardiogram of the heart to be scanned comprises:

in response to a determination that a product between a moving speed of a scanning bed and a difference obtained by subtracting data collection time of the medical imaging apparatus from the RR interval of the heart is greater than the scanning coverage range for the medical imaging apparatus scanning with the candidate slice configuration, determining the number of RR intervals being 1; and in response to a determination that a product between the moving speed of the scanning bed and the difference obtained by subtracting the data collection time of the medical imaging apparatus from the RR interval of the heart is less than or equal to the scanning coverage range for the medical imaging apparatus scanning with the candidate slice configuration, determining the number of RR intervals being 2.

11. The method of claim 1, wherein determining the maximum and minimum values of the scanning time for scanning the heart with the candidate slice configuration according to the determined number of RR intervals, the expected number of steps, and the RR interval of the heart comprises:

determining the maximum value of the scanning time for scanning the heart with the candidate slice configuration according to a formula represented by:

$$scanTime_{max} = nStepCount_i \times RRInterval \times RRCount + T;$$

determining the minimum value of the scanning time for scanning the heart with the candidate slice configuration according to a formula represented by:

$$scanTime_{min} = nStepCount_i \times RRInterval \times RRCount - RRInterval + T;$$

wherein $scanTime_{max}$ represents the maximum value of the scanning time for the medical imaging apparatus scanning the heart to be scanned with the candidate slice configuration;

$scanTime_{min}$ represents the minimum value of the scanning time for the medical imaging apparatus scanning the heart to be scanned with the candidate slice configuration;

$nStepCount_i$ represents the expected number of steps for the medical imaging apparatus scanning the heart to be scanned with the candidate slice configuration;

RRInterval represents the RR interval of the heart to be scanned displayed on the electrocardiogram;

RRCount represents the number of RR intervals in which the medical imaging apparatus completes one scan for scanning the heart to be scanned with the candidate slice configuration; and T represents a data collection time of the medical imaging apparatus.

12. A medical imaging apparatus, comprising:
a processor; and
a machine-readable storage medium in which machine-executable instructions corresponding to a control logic of selecting a slice configuration of the medical imaging apparatus executable by the processor are stored,
wherein by executing the machine-executable instructions enables the processor to:
when a region to be scanned is a heart, determine maximum and minimum values of scanning time for scanning the heart by the medical imaging apparatus with each of a plurality of candidate slice configurations according to a length of the heart and an electrocardiogram of the heart;
select one or more first slice configurations for each of which the maximum value of the scanning time is less than a preset time threshold from the plurality of candidate slice configurations;
determine an expected scanning length for scanning the region to be scanned with each of the first slice configurations according to a scanning coverage range for scanning the region to be scanned with each of the first slice configurations and a length of the region to be scanned;
determine an expected redundant scanning dose for scanning the region to be scanned with each of the first slice configurations according to the expected scanning length for scanning the region to be scanned with each of the first slice configurations and the length of the region to be scanned; and
select a target slice configuration to scan the region to be scanned;
wherein determining the maximum and minimum values of the scanning time for scanning the heart with each of the plurality of candidate slice configurations according to the length of the heart and the electrocardiogram of the heart comprises:
for each of the plurality of candidate slice configurations,
determining, by the medical imaging apparatus, a number of RR intervals in which the medical imaging apparatus completes one scan with the candidate slice configuration according to the electrocardiogram of the heart:
determining, by the medical imaging apparatus, an expected number of steps according to a scanning coverage range for the medical imaging apparatus scanning with the candidate slice configuration and the length of the heart:
determining, by the medical imaging apparatus, a RR interval of the heart displayed on the electrocardiogram; and
determining, by the medical imaging apparatus, the maximum and minimum values of the scanning time for scanning the heart with the candidate slice configuration according to the determined number of RR intervals, the expected number of steps, and the RR interval of the heart.

13. The medical imaging apparatus according to claim 12, wherein when determining the expected scanning length for scanning the region to be scanned with a first slice configuration, the machine-executable instructions enable the processor to:
determine the scanning coverage range for the medical imaging apparatus scanning with the first slice configuration according to a scanning field of view of the medical imaging apparatus;
determine an expected number of steps for scanning the region to be scanned with the first slice configuration according to the scanning coverage range for scanning with the first slice configuration and the scanning length of the region to be scanned; and
determine the expected scanning length for scanning the region to be scanned with the first slice configurations according to the scanning coverage range and the expected number of steps for scanning the region to be scanned with the first slice configurations.

14. The medical imaging apparatus according to claim 12, wherein when selecting a slice configuration according to the redundant scanning dose, the machine-executable instructions enable the processor to:
select a first slice configuration having a minimum redundant scanning dose as a first target slice configuration to scan previous (nStepCount-1) steps of all the expected number of steps nStepCount; and
select a second slice configuration having a minimum scanning coverage range as a second target slice configuration to scan a last step of all the expected number of steps to be scanned.

15. The medical imaging apparatus according to claim 14, wherein when selecting the second slice configuration having the minimum scanning coverage range as the second target slice configuration to scan the last step of all the expected number of steps to be scanned, the machine-executable instructions enable the processor to:
  determine a scanning length to be scanned in the last step according to an expected scanning length of the previous (nStepCount-1) steps for scanning the region to be scanned with the first target slice configuration and the scanning length of the region to be scanned;
  select one or more second slice configurations for each of which a scanning coverage range is greater than or equal to the scanning length to be scanned in the last step; and
  select a second slice configuration having the minimum scanning coverage range from the second slice configurations as the second target slice configuration to scan the last step.

16. The medical imaging apparatus according to claim 12, wherein the region to be scanned is the heart,
  when determining the expected scanning time for scanning the region to be scanned with each of the plurality of candidate slice configurations according to the scanning length of the region to be scanned, the machine-executable instructions enable the processor to: determine the maximum and minimum values of the scanning time of the medical imaging apparatus for scanning the region to be scanned with each of the plurality of candidate slice configurations according to the length of the heart to be scanned and the electrocardiogram of the heart to be scanned; and
  when selecting one or more first slice configuration for each of which the scanning time is less than a preset time threshold from the plurality of candidate slice configurations, the machine-executable instructions enable the processor to: select one or more first slice configurations for each of which the maximum value of the expected scanning time is less than the preset time threshold from the plurality of candidate slice configurations.

17. A machine-readable storage medium in which machine-executable instructions executable by one or more processors are stored, wherein the machine-executable instructions enable the processor to perform a method of selecting a slice configuration of a medical imaging apparatus, the method comprising:
  when a region to be scanned is a heart, determining, by the medical imaging apparatus, maximum and minimum values of scanning time for scanning the heart by the medical imaging apparatus with each of a plurality of candidate slice configurations according to a length of the heart and an electrocardiogram of the heart;
  selecting, by the medical imaging apparatus, one or more first slice configurations for each of which the maximum value of the scanning time is less than a preset time threshold from the plurality of candidate slice configurations;
  determining, by the medical imaging apparatus, an expected scanning length for scanning the region with each of the first slice configurations;
  determining, by the medical imaging apparatus, an expected redundant scanning dose for scanning the region with each of the first slice configurations according to the expected scanning length for scanning the region with each of the first slice configurations and a scanning length of the region; and
  selecting, by the medical imaging apparatus, a target slice configuration according to the redundant scanning dose for scanning the region with each of the first slice configurations, wherein the region is to be scanned by the medical imaging apparatus with the target slice configurations;
  wherein determining the maximum and minimum values of the scanning time for scanning the heart with each of the plurality of candidate slice configurations according to the length of the heart and the electrocardiogram of the heart comprises:
    for each of the plurality of candidate slice configurations,
      determining, by the medical imaging apparatus, a number of RR intervals in which the medical imaging apparatus completes one scan with the candidate slice configuration according to the electrocardiogram of the heart;
      determining, by the medical imaging apparatus, an expected number of steps according to a scanning coverage range for the medical imaging apparatus scanning with the candidate slice configuration and the length of the heart:
      determining, by the medical imaging apparatus, a RR interval of the heart displayed on the electrocardiogram; and
      determining, by the medical imaging apparatus, the maximum and minimum values of the scanning time for scanning the heart with the candidate slice configuration according to the determined number of RR intervals, the expected number of steps, and the RR interval of the heart.

* * * * *